United States Patent
Laffitte et al.

(10) Patent No.: US 11,534,743 B2
(45) Date of Patent: Dec. 27, 2022

(54) ACID COMPOSITION FOR PROCESSING FATTY ACIDS

(71) Applicant: ARKEMA FRANCE, Colombes (FR)

(72) Inventors: Jean-Alex Laffitte, Pau (FR); Bernard Monguillon, Bayonne (FR); Vijay Srinivas, Exton, PA (US)

(73) Assignee: ARKEMA FRANCE, Colombes (FR)

( * ) Notice: Subject to any disclaimer, the term of this patent is extended or adjusted under 35 U.S.C. 154(b) by 432 days.

(21) Appl. No.: 16/463,534

(22) PCT Filed: Nov. 20, 2017

(86) PCT No.: PCT/FR2017/053172
§ 371 (c)(1),
(2) Date: May 23, 2019

(87) PCT Pub. No.: WO2018/096248
PCT Pub. Date: May 31, 2018

(65) Prior Publication Data
US 2019/0374931 A1    Dec. 12, 2019

Related U.S. Application Data

(60) Provisional application No. 62/426,334, filed on Nov. 25, 2016.

(30) Foreign Application Priority Data

Nov. 25, 2016   (FR) ..................................... 1661482

(51) Int. Cl.
*B01J 31/02* (2006.01)
*C07C 67/03* (2006.01)

(52) U.S. Cl.
CPC ........... *B01J 31/0225* (2013.01); *C07C 67/03* (2013.01); *B01J 2231/49* (2013.01)

(58) Field of Classification Search
CPC .............................. B01J 31/0225; C07C 67/03
See application file for complete search history.

(56) References Cited

U.S. PATENT DOCUMENTS

| | | | |
|---|---|---|---|
| 4,695,411 A | 9/1987 | Stern et al. | |
| 9,758,479 B2 | 9/2017 | Maj et al. | |
| 2011/0245522 A1 | 10/2011 | Wu et al. | |
| 2016/0251289 A1 | 9/2016 | Laffitte et al. | |

FOREIGN PATENT DOCUMENTS

| | | | |
|---|---|---|---|
| CN | 1760336 | 4/2006 | |
| CN | 105593209 | 5/2006 | |
| CN | 1830949 A | 9/2006 | |
| CN | 101074391 A | 11/2007 | |
| CN | 101955850 A | 1/2011 | |
| DE | 538762 | 11/1931 | |
| DE | 10 2004 007 776 A1 | 9/2005 | |
| EP | 0 072 980 A1 | 3/1983 | |
| EP | 0 194 165 A1 | 9/1986 | |
| EP | 0 605 279 A1 | 7/1994 | |
| EP | 0605279 A1 * | 7/1994 | ............ B01J 35/023 |
| EP | 1 951 852 B1 | 4/2016 | |
| FR | 2929621 | 10/2009 | |
| JP | H06-277523 | 10/1994 | |
| KR | 10-2016-0130421 | 11/2016 | |
| WO | 2006/081644 A2 | 8/2006 | |
| WO | 2015/018996 A1 | 2/2015 | |
| WO | 2015/134495 A1 | 9/2015 | |

OTHER PUBLICATIONS

Hayyan et al., Bioenerg. Res., (2015), v8, p. 459-463. (Cited in Applicant's IDS).*
International Search Report for PCT/FR2017/053172, dated Feb. 7, 2018 (6 pages with English translation).
Written Opinion for PCT/FR2017/053172, dated Feb. 7, 2018 (7 pages).
Korean Office Action dated Nov. 9, 2020 for Korean Patent Application No. 10-20197-017950 (7 Pages, with English translation).
Chinese Office Action dated Apr. 23, 2021 for Chinese Patent Application No. 201780073006.3 (4 Pages, with English translation).
Chinese Search Report dated Apr. 14, 2021 for Chinese Patent Application No. 201780073006.3 (2 Pages).
International Preliminary Report on Patentablity for International Patent Application No. PCT/FR2017/053172 dated May 28, 2019 (8 pages in French with English Translation).
Avhad, M. R., et al. A review on recent advancement in catalytic materials for biodiesel production. Renewable and Sustainable Energy Reviews. 2015. vol. 50, pp. 696-718.
Aranda, D.A.G., et al. Acid-Catalyzed Homogeneous Esterification Reaction for Biodiesel Production from Palm Fatty Acids. Catalysis Letters. 2008 .vol. 122, No. 1-2, pp. 20-25.
Hayyan, A., et al. Ethanesulfonic acid-based esterification of industrial acidic crude palm oil for biodiesel production. Bioresource Technology. 2011. vol. 102, No. 20, pp. 9564-9570.

* cited by examiner

*Primary Examiner* — Yong L Chu
(74) *Attorney, Agent, or Firm* — Smith, Gambrell & Russell, LLP; Dennis C. Rodgers; Ram W. Sabnis

(57) ABSTRACT

The invention relates to a composition comprising:
at least one alkane-sulphonic acid R—SO$_3$H wherein R represents a saturated, linear or branched, hydrocarbon chain comprising from 1 to 4 carbon atoms, which can or cannot be substituted by at least one halogen atom;
sulphuric acid;
and optionally at least one solvent;
of which the proportions are defined in the description.
The invention also relates to the use of the composition as a fatty acid esterification catalyst.

16 Claims, 1 Drawing Sheet

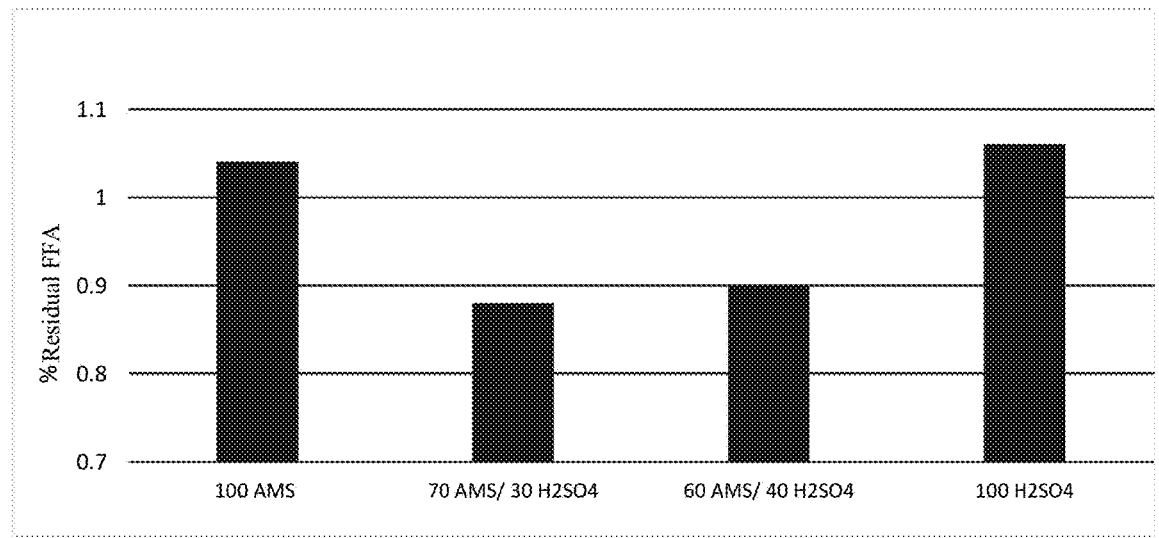
-- Figure 1 --
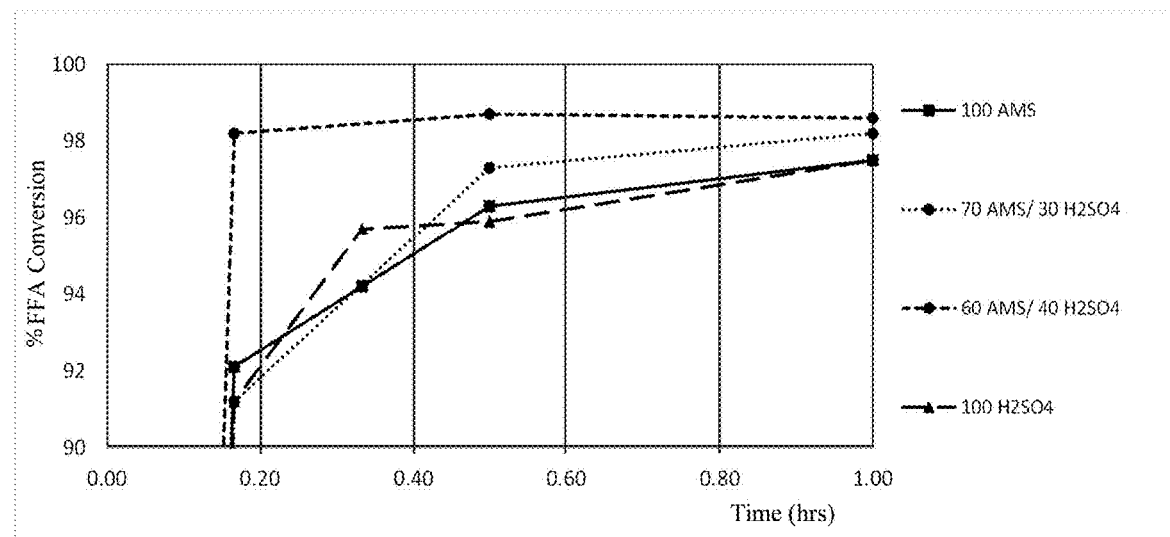
-- Figure 2 --

ACID COMPOSITION FOR PROCESSING FATTY ACIDS

The invention relates to the processing of fatty acids, particularly fatty acid esterification. The fatty acid esters obtained can thus be used as raw materials in various areas such as cosmetics or biofuel production. In particular, the invention relates to a composition of acids which can be used as a catalyst in fatty acid esterification methods.

In the esterification of fatty acids, it is often necessary to use a catalyst, for example an acid. Sulphuric acid is one of the known acidic catalysts used.

For example, patent EP1951852 B1 relates to a method for manufacturing fatty acid alkyl esters from "tall oil" containing sulphur compounds in the presence of a strong acidic catalyst such as sulphuric acid in particular.

Sulphuric acid is known for its oxidising and dehydrating action that leads to secondary reactions that can compete with the main esterification reaction.

The use of alkane-sulphonic acid is also known as an acid catalyst in fatty acid esterification reactions. Thus, WO2006081644 and WO2015134495 describe the use of methane-sulphonic acid in fatty acid esterification methods.

However, as alkane-sulphonic acids are relatively expensive compounds, ways to optimise their use are being sought. Furthermore, it can be helpful to further improve the efficacy of esterification catalysts.

It is therefore necessary to find an acid catalyst that is more effective, both in terms of the degree of conversion of fatty acids to esters and from the perspective of esterification kinetics, and which is inexpensive. To this end, the Applicant has demonstrated that a catalyst comprising at least one particular acidic composition enables, among other things, these drawbacks to be overcome.

Thus, and according to a first aspect, the present invention relates to a composition comprising:
- at least one alkane-sulphonic acid of formula $R-SO_3H$ wherein R represents a saturated, linear or branched, hydrocarbon chain comprising from 1 to 4 carbon atoms, which can or cannot be substituted by at least one halogen atom;
- sulphuric acid;
- and optionally at least one solvent;

wherein:
- the proportion by weight of alkane-sulphonic acid in relation to the total weight of the alkane-sulphonic acid and sulphuric acid is comprised between 40% and 90%, preferably 44% and 89%;
- the proportion by weight of sulphuric acid in relation to the total weight of the alkane-sulphonic acid and sulphuric acid is comprised between 10% and 60%, preferably 11% and 56%.

The solvent can be any type known to the person skilled in the art and for example water, organic solvent, a blend of organic solvents, or a mixture of water and one or more organic solvents.

In one embodiment, the solvent is chosen among water, alcohol and ether, preferably water and a $C_1$ to $C_3$ alcohol, and more particularly water and methanol, alone or in combination. The proportion by weight of solvent relative to the total weight of the composition is typically comprised within a range of from 0% to 50%, preferably from 5% to 35%.

When the hydrocarbonated chain of the R group above is substituted by at least one halogen atom, said halogen atom is preferably chosen among fluorine, chlorine and bromine, preferably fluorine.

Alkane-sulphonic acid, of formula $R-SO_3H$ as previously defined, that can be used in the present invention is advantageously chosen among methane-sulphonic acid, ethane-sulphonic acid, n-propane-sulphonic acid, iso-propane-sulphonic acid, n-butane sulphonic acid, iso-butane sulphonic acid, sec-butane sulphonic acid, tert-butane sulphonic acid, trifluoro-methane-sulphonic acid (also known as triflic acid), and mixtures of two or more of them in any proportions, and particularly preferably the alkane-sulphonic acid is methane-sulphonic acid.

Moreover, the acid composition according to the present invention can comprise one or more additives and/or filler(s), well-known to the person skilled in the art, such as those chosen, for example, among the corrosion inhibitors, fragrances, odorising agents, etc.

The present invention also relates to the use of said composition as an esterification catalyst, and more particularly in the esterification of fatty acid(s).

Finally, the invention relates to a method for manufacturing fatty acid esters comprising the following steps:
a/ introducing least one fatty acid into a reactor;
b/ adding at least one alcohol;
c/ heating the reaction medium;
d/ introducing the previously-defined acid composition as a catalyst
e/ optionally, removing the water formed during the esterification reaction; and
f/ recovering the fatty acid ester;
with step d being optionally performed at the same time as step a and/or step b, preferably at the same time as steps a and/or b.

In said method, the catalyst/fatty acid molar ratio is comprised within a range of from 0.001 to 1, preferably from 0.01 to 0.5 and more particularly from 0.02 to 0.2.

The invention will be better understood by the following description, figures, and examples but is not limited to these figures and examples.

FIG. 1 represents the percentage of residual fatty acids (ordinate axis) in the organic phase after the esterification reaction depending on the nature of the acid catalyst used.

FIG. 2 represents the conversion kinetics of residual fatty acids during the esterification stage depending on the nature of the acid catalyst used.

In FIGS. 1 and 2:
- 100 MSA means that the catalyst used comprises 70% pure methane-sulphonic acid and 30% water,
- 70 MSA/30 $H_2SO_4$ means that the catalyst used is a catalyst according to the invention and that it comprises:
  - 49% by weight of pure methane-sulphonic acid relative to the total weight of the mixture;
  - 29.1% by weight of pure sulphuric acid relative to the total weight of the mixture; and
  - 21.9% water.
- 60 MSA/40 $H_2SO_4$ means that the catalyst used is a catalyst according to the invention and comprises:
  - 42% by weight of pure methane-sulphonic acid relative to the total weight of the mixture;
  - 38.8% by weight of pure sulphuric acid relative to the total weight of the mixture; and
  - 19.2% water.
- 100 $H_2SO_4$ means the catalyst used comprises 97% pure sulphuric acid and 3% water.

The MSA used is MSA diluted to 70% by weight in water and the sulphuric acid used is a sulphuric acid diluted to 97% by weight in water.

More specifically, the invention relates to a composition comprising:
- at least one alkane-sulphonic acid of formula R—SO$_3$H wherein R represents a saturated, linear or branched, hydrocarbon chain comprising from 1 to 4 carbon atoms, which can or cannot be substituted by at least one halogen atom, and
- sulphuric acid.

In the composition according to the invention:
- the weight proportion of pure alkane-sulphonic acid in relation to the total weight of the alkane-sulphonic acid and sulphuric acid is comprised within a range of from 40% to 90%; and
- the proportion by weight of pure sulphuric acid in relation to the total weight of the alkane-sulphonic acid and sulphuric acid is comprised within a range of from 10% to 60%.

Preferably:
- the proportion by weight of pure alkane-sulphonic acid in relation to the total weight of the alkane-sulphonic acid and sulphuric acid is comprised within a range of from 44% to 89%; and
- The proportion by weight of pure sulphuric acid in relation to the total weight of the alkane-sulphonic acid and sulphuric acid is comprised within a range of from 11% to 56%.

"Pure" means an undiluted compound in water or solvent.

With the composition according to the invention, the Applicant demonstrated surprising results, such as those provided as examples in this application.

It should be noted that this composition can also comprise one or more solvents, and optionally one or more additives.

"Solvent" means aqueous, organic or water-soluble products. Preferably, the solvent can be water, alcohol or ether, taken alone or in combination. Preferably, the solvent is water and/or a C1 to C3 alcohol. More particularly, the solvent is water, methanol or a water/methanol mixture. The content by weight of solvent relative to the total weight of the composition is comprised within a range of from 0% to 50%, and preferably from 5% to 35%.

When the hydrocarbonated chain of the R group above is substituted by at least one halogen atom, said halogen atom is chosen among fluorine, chlorine and bromine, preferably fluorine.

Preferably, the alkane-sulphonic acid comprised in the composition according to the invention is chosen among methane-sulphonic acid, ethane-sulphonic acid, n-propane-sulphonic acid, iso-propane-sulphonic acid, n-butane sulphonic acid, iso-butane sulphonic acid, sec-butane sulphonic acid, tert-butane sulphonic acid, trifluoromethanesulphonic acid (also known as triflic acid), and mixtures of two or more of them in any proportions. Preferably, the alkane-sulphonic acid is methane-sulphonic acid.

Said at least one alkane-sulphonic acid can be used as it is, or in combination with one or more other components, that is to say in a formulation. Any type of formulation comprising at least one alkane-sulphonic acid may be suitable. As a general rule, the formulation comprises from 0.01% to 100% by weight of alkane-sulphonic acid, more generally from 0.05% to 90% by weight, in particular from 0.5% to 75% by weight, limits included, of alkane-sulphonic acid(s), relative to the total weight of said alkane-sulphonic acid formulation.

The formulation is, for example, an aqueous, organic or hydro-organic formulation. The formulation can be prepared in the form of a concentrated mixture, said concentrated mixture optionally being diluted prior to final use. Finally, within the meaning of the present invention, the formulation can be a pure alkane-sulphonic acid, or a mixture of pure alkane-sulphonic acids, i.e., the formulation can contain only one or more alkane-sulphonic acids, without any other additive to the formulation or any other solvent or diluent.

According to one embodiment of the invention, the alkane-sulphonic acid can be diluted to 70% in a solvent, preferably in water. Preferably, the alkane-sulphonic acid is methane-sulphonic acid diluted to 70% by weight in water, such as the one found on the market. For example, anhydrous methane-sulphonic acid (AMSA) can be used, or methane-sulphonic acid in aqueous solution, such as a 70% methane-sulphonic acid solution in water and marketed by Arkema under the brand name Scaleva®. A methane-sulphonic acid marketed by Arkema is also available under the name "MSA LC".

An aqueous solution of methane-sulphonic acid can also be used, such as that marketed by B.A.S.F under the name Lutropur®MSA in ready-to-use form or diluted with water in the proportions indicated above.

For the sulphuric acid formulation, any type of formulation can be suitable. As a general rule, the formulation comprises from 0.01% to 100% by weight of sulphuric acid, more generally from 0.05% to 98% by weight, in particular from 74% to 97% by weight, limits included, of sulphuric acid, relative to the total weight of said formulation.

The formulation is, for example, an aqueous, organic or hydro-organic formulation. The formulation can be a concentrated mixture. Alternatively, the formulation can also be a ready-to-use formulation, i.e., one that does not need to be diluted. Finally, within the meaning of the present invention, the formulation can be pure sulphuric acid without any further additive to the formulation or any other solvent or diluent. Preferably, the sulphuric acid is diluted to 97% by weight in water, such as that marketed by Arkema or the sulphuric acid diluted to 96% by weight in water marketed by BASF.

According to a preferred embodiment, the composition according to the invention is used as an acid esterification catalyst and preferably as a fatty acid esterification catalyst.

The present invention also relates to an esterification acid catalyst, preferably a fatty acid esterification, comprising, and preferably consisting of, the acidic composition as previously defined.

The composition according to the invention is particularly useful as a catalyst, such as a catalyst for the esterification of fatty acids, either pure or combined with oils or fats, which are then called "free fatty acids", as opposed to fatty acids in the form of mono-, di- and/or tri-glycerides present in said oils and/or fats.

The fatty acid esterification reaction enables, from the condensation of an alcohol on a fatty carboxylic acid, a fatty ester and a water molecule to be obtained. "Fatty acid" means an aliphatic-chain carboxylic acid in particular in $C_4$-$C_{36}$. Natural fatty acids usually have a carbon chain of from 4 to 36 carbon atoms, with said carbon chain possibly being saturated or unsaturated, linear, or branched.

According to the invention, the fatty acids can preferably be fatty acids present in oils. In this case, the esterification reaction can be followed by a transesterification reaction in the presence of a light alcohol, typically comprising from 1 to 4 carbon atoms, to obtain esters of fatty acids and glycerol, said fatty acid esters then being usable as fuel known as "biodiesel".

Typically, when preparing biodiesel, if the level of residual fatty acid present is in the oil or grease is greater than 1%, there is a risk of saponification of said residual fatty acids by reaction with the transesterification catalysts. This can be a drawback when producing biodiesel, as the soaps formed can create an emulsion and make the separation of the biodiesel and glycerol difficult or impossible.

The Applicant has thus demonstrated that, compared with alkane-sulphonic acid alone as a catalyst or compared with sulphuric acid alone as catalyst, the mixture of at least one alkane-sulphonic acid with sulphuric acid in the proportions claimed enables, after an esterification step, the level of residual fatty acids in the organic phase to be reduced to less than 1.1% weight, preferably 1% weight, and more particularly 0.95% weight, which is very difficult to achieve with alkane-sulphonic acid alone or sulphuric acid alone.

This low residual fatty acid content notably offers an advantage with regard to the final purity of the ester or in the transesterification step, often performed later, since the latter will consume less catalyst, usually basic catalyst, which is often expensive, and will limit the formation of soaps that disrupt the reaction.

It has also been shown that the use of the acid composition according to the invention as an esterification catalyst results in a lower amount of residual catalyst in the organic phase than that obtained with the alkane-sulphonic acid catalyst alone or the sulphuric acid catalyst alone. This reduces the basic catalyst consumption in any subsequent transesterification in view of the production of biodiesel, for example.

Surprisingly, it has also been demonstrated that the use of the composition according to the invention improves the conversion kinetics of fatty acids compared to the use of an alkane-sulphonic acid alone or sulphuric acid alone.

According to an embodiment of the invention, the composition according to the invention is an esterification and transesterification catalyst, thereby allowing for single-step esterification and transesterification of free fatty acids and fatty acids in the form of mono-, di- and/or tri-glycerides.

Optionally, the composition according to the invention can comprise one or more additives well-known to the person skilled in the art, such as those selected from corrosion inhibitors, fragrances, odorising agents, and other additives known to the person skilled in the art.

According to a preferred embodiment, the composition according to the invention comprises at least one corrosion inhibitor. According to another preferred embodiment, the composition comprises at least one fragrance and/or odorising agent.

The composition according to the invention can be prepared by mixing alkane-sulphonic acid(s) and sulphuric acid, according to any method known to the person skilled in the art, such as, but not limited to, the following method.

The alkane-sulphonic acid is placed in a container that has been cooled to approximately 10° C. The sulphuric acid is then added according to any method known to the person skilled in the art, so as to limit any exothermicity of the reaction. In general, the addition of sulphuric acid will be performed so that the temperature does not exceed 90° C., preferably 80° C. and more particularly 60° C. If a solvent and any additives are used, it is preferable to pre-mix them with the alkane-sulphonic acid before slowly adding the sulphuric acid. Depending on the solvent and additives used, the sulphuric acid will be added at a rate that prevents the mixture from reaching a temperature greater than 90° C. preferably 80° C. and more particularly 60° C.

The present application also concerns a method for manufacturing fatty acid esters wherein the fatty acids are esterified in the presence of the composition according to the invention.

The esterification method consists of placing a fatty acid or a mixture of fatty acids into a reactor. Alcohol is then added and the medium is heated to a temperature generally comprised within a range of from 50° C. to 200° C., more generally from 60° C. to 120° C., and preferably from 60° C. to 80° C. The composition according to the invention is preferably injected at the esterification temperature. According to another embodiment of the invention, said composition can be added before heating.

According to yet another embodiment of the invention, the alcohol and said composition can be added continuously, together or separately, when the medium has reached the esterification temperature. According to one embodiment of the invention, said composition can be added with the fatty acid or the fatty acid mixture.

According to a preferred embodiment of the invention, the fatty acid or fatty acid mixture, the alcohol and said composition are added together before heating. The esterification reaction is then performed within the previously-indicated temperature range.

During this esterification method, the composition according to the invention acts as catalyst.

The fatty acids can be of any type chosen from the fatty acids and fatty acid mixtures known to the person skilled in the art, including fatty acids from vegetal or animal environments, including seaweed, and more generally from the vegetable kingdom. These acids usually and advantageously comprise least one olefinic non-saturation.

Said acids are most commonly present in vegetable oils extracted from various oilseed plants such as, but not limited to, peanuts, sunflower, rapeseed, castor, Lesquerella, olives, soybeans, oil palms, avocados, nuts, hazelnuts, almonds, sesame, sea-buckthorn, and meadowfoam, including seaweed.

They can also be obtained from land or sea animals, and in the latter case they can be obtained from mammal or fish fats, such as, but not limited to, fats from cattle, cod, whales, or seals. Finally, these acids can come from recycled used oils such as, but not limited to, used cooking oil.

As described previously, the acids in these oils are brought together with alcohol. The alcohol can be any type known to the person skilled in the art, such as the mono-alcohols, diols, triols, tetrols, etc., used alone or in combination. Preferably, the alcohol has a molar mass comprised within a range of from 30 to 200 g/mol$^{-1}$.

According to one embodiment of the invention, the alcohol is of the $R^1$—OH type, where $R^1$ is an alkyl or aromatic, linear or branched, saturated or unsaturated chain comprising from 1 to 20 carbon atoms. Preferably, $R^1$ is a alkyl chain comprising from 1 to 10 carbon(s), particularly from 1 to 4. According to another embodiment of the invention, the alcohol has more than one —OH function, for example, two or three —OH functions, and, for example, the alcohol can be glycerol (propane-1,2,3-triol).

In one embodiment of the invention where the acid composition is used as a fatty acid esterification reaction catalyst, and in particular for free fatty acids in oils, the molar ratio of the catalyst according to the invention to the fatty acids is comprised within a range of from 0.001 to 1, preferably from 0.01 to 0.5 and more particularly from 0.02 to 0.2. The number of moles of fatty acids is measured by acid-basic potentiometry assay and is expressed as moles per gram of fatty acids present in the starting product. This value is then multiplied by the molar ratio of the catalyst to the fatty acids to determine the amount of catalyst to be added.

According to one embodiment of the esterification method according to the invention, the alcohol/fatty acid molar ratio is comprised within a range of from 1 to 20, preferably from 4 to 10.

According to one embodiment of the invention, the fatty acid esterification reaction can be performed at any temperature but preferably at temperatures comprised within a range of from 50° C. to 200° C., more generally at temperatures of from 60° C. to 120° C., preferably from 60° C. to 80° C.

According to one embodiment of the invention, the fatty acid esterification reaction can be performed at any pressure but preferably at a pressure comprised within a range of from $10^3$ Pa (0.01 bar absolute) to $2.10^6$ Pa (20 bar absolute), more generally from atmospheric pressure to $10^6$ Pa (10 bar absolute) and most preferably under atmospheric pressure.

The reaction time for fatty acid esterification can vary considerably and is usually comprised within a range of from a few minutes to a few hours, for example from 10 minutes to 6 hours, typically from 30 minutes to 180 minutes.

The esterification reaction can be performed in batches or on a continuous basis. The catalyst according to the invention is added to the mixture or separately to the reaction medium. It can be added alone or in co-feed with the source of fatty acids (oil, animal fat, etc.) and/or the alcohol. The reaction can be performed in one to or more reactors, comprised within a range of from 2 to 15, typically from 2 to 10 reactors, more typically from 2 to 5 reactors, arranged in parallel or cascaded. According to a particular embodiment, the batch method is preferred with several cascaded reactors.

It can be advantageous to carry out organic and aqueous phase separations between two reactors. In order to improve the reaction yield, the water that forms can be disposed of according to any method known to the person skilled in the art, for example as it is formed, and for example, by heating. In one embodiment of the invention, removing the water can result in the removal of all or part of the solvent, particularly if the solvent is an alcohol.

According to one embodiment of the invention, the free fatty acids used come from vegetable oil to obtain biofuel, including biodiesel. In this case biodiesel is obtained after a transesterification step as described above. If a neutralization step of this biodiesel is necessary, the aqueous acid phase obtained at the end of the free fatty acid esterification reaction can be used. According to one embodiment of the invention, the alcohol is removed before using said acid phase.

The fatty acid esterification reaction according to the invention also provides products that can be used in various fields, such as cosmetics, lubricants, agrochemistry, pharmaceuticals, cleaning, etc.

EXAMPLES

The following examples illustrate the present invention but are not limiting under any circumstances.

Method for Preparing a Composition According to the Invention:

A composition is prepared, comprising:
  60% by weight of methane-sulphonic acid diluted to 70% in water (i.e., 42% by weight of pure methane-sulphonic acid);
  40% by weight of sulphuric acid diluted to 97% in water (i.e., 39% by weight of pure sulphuric acid).

The above composition is prepared from a 70% by weight aqueous MSA LC solution from Arkema, which is placed in a double envelope reactor cooled by a thermostatic bath set at 10° C. Sulphuric acid at 97% by weight is added, by drip, using a casting bulb attached to the double envelope reactor bonnet, taking care to not exceed 60° C.

The resulting composition contains, for 100 g of composition, 0.8355 moles of acids (42/96+39/98 (96 being the molar mass of the MSA and 98 being the molar mass of $H_2SO_4$)). The molar mass of the acid mixture is 119.7 g/mole (=100/0.8355).

The composition thus prepared is used as an esterification catalyst in the example below.

Example of Esterification of an Oil

An industrial blend is used, consisting of an oil comprising triglycerides and 94% by weight of free fatty acids (FFA) with a mean molecular weight of fatty acids of 268±1 g/mol.

The molar methanol/FFA ratio is 8. The molar ratio of the catalyst to the FFA is equal to 0.175.

In a double-envelope reactor preheated to 50° C. and equipped with mechanical stirring, temperature probe and refrigerant, 451 g of said industrial blend comprising triglycerides and 94% by weight of FFA, i.e., 1.582 moles of fatty acid, is injected. The amount of methanol injected is determined as follows: 1.582×8×32=405 g methanol (8 molar equivalents/FAA).

The reaction mixture is heated to 70° C. and then the catalyst prepared above is injected. The amount of catalyst to be added is calculated as follows: 1.582×0.175× 119.7=33.14 g of composition (0.175 molar equivalent/ FFA). The reaction medium is stirred for 2 hours at 70° C., and then decanted and left to settle overnight at 70° C. The aqueous and organic phases are analysed according to the methods described below.

Analysis Methods:

The FFA and catalyst, in the organic phase, are assayed by potentiometry as follows: about 1.5 g of organic phase is placed in a beaker which is then filled up to 50 Ml with the toluene/isopropanol/water mixture in a proportion of 500/ 495/5 by volume.

The potentiometric assay is performed with KOH 0.1 mol/L$^{-1}$ 1 in ethanol with an DG113-SC #2 electrode and a T50 titrator, both from Mettler Toledo.

The dosage makes it possible to determine accurately, on the one hand, the amount of residual catalyst in the organic phase in moles per gram, and on the other hand the residual fatty acids content of the organic phase in % by weight.

The acid-base assay enables 2 potential jumps to be obtained: the first jump corresponds to the catalyst and the second jump corresponds to the residual fatty acids.

Results:

The assays described above measure the percentage of residual FFA in the organic phase.

These results, shown in FIG. 1, show that the mass percentage of residual FFA is 1.2 with MSA alone, 1.05 with $H_2SO_4$ only, 0.89 with the 70 MSA/30 $H_2SO_4$ composition according to the invention, and 0.9 with the 60 MSA/40 $H_2SO_4$ composition according to the invention.

The composition according to the invention results in a percentage of residual FFA lower than those obtained with the other compositions.

Moreover, the FFA conversion kinetics is improved compared to the use of each acid alone, as shown in FIG. 2. Indeed, it was found that the composition according to the invention resulted in faster ester conversion kinetics and, over the same time period (1 hour), improved FFA conversion (98% with the composition according to the invention and 97% with MSA alone and $H_2SO_4$ alone).

The invention claimed is:

1. A composition comprising:
one or more alkane-sulphonic acids of formula $R-SO_3H$ wherein R represents a saturated, linear or branched, hydrocarbon chain comprising from 1 to 4 carbon atoms;
sulphuric acid;
and optionally at least one solvent;
wherein:
the proportion by weight of alkane-sulphonic acid in relation to the total weight of the alkane-sulphonic acid and sulphuric acid is comprised between 40% and 90%;
the proportion by weight of sulphuric acid in relation to the total weight of the alkane-sulphonic acid and sulphuric acid is comprised between 10% and 60%;
the proportion by weight of solvent relative to the total weight of the composition is comprised between 0% and 50%; and
the one or more alkane-sulphonic acids comprises methane-sulphonic acid.

2. The composition according to claim 1 wherein the solvent is chosen among water, alcohol and ether, alone or in combination.

3. The composition according to claim 1 wherein the solvent is water or a $C_1$ to $C_3$ alcohol, alone or in combination.

4. The composition according to claim 1 wherein the solvent is water or methanol, alone or in combination.

5. The composition according to claim 1 wherein the proportion by weight of solvent relative to the total weight of the composition is comprised between 5% and 35%.

6. A composition according to claim 1, wherein the composition further comprises at least one corrosion inhibitor.

7. A composition according to claim 1 comprising at least one fragrance or one odorising agent, alone or in combination.

8. A method for manufacturing fatty acid esters comprising the following steps:
a/ placing at least one fatty acid into a reactor;
b/ adding at least one alcohol;
c/ heating the reaction medium;
d/ introducing the composition according to claim 1 as a catalyst;
e/ optionally, removing the water formed during the esterification reaction; and
f/ recovering the fatty acid esters
with step d being optionally performed at the same time as step a and/or step b.

9. The method according to claim 8 wherein the catalyst/fatty acid molar ratio is comprised within a range of from 0.001 to 1.

10. The composition according to claim 1, wherein the proportion by weight of alkane-sulphonic acid in relation to the total weight of the alkane-sulphonic acid and sulphuric acid is comprised between 44% and 89%, and wherein the proportion by weight of sulphuric acid in relation to the total weight of the alkane-sulphonic acid and sulphuric acid is comprised between 11% and 56%.

11. The composition according to claim 10, wherein the proportion by weight of solvent relative to the total weight of the composition is comprised between 5% and 35%.

12. The method of claim 8 wherein step d is performed at the same time as step a and/or step b.

13. The method according to claim 8 wherein the catalyst/fatty acid molar ratio is comprised within a range of from 0.01 to 0.5.

14. The method according to claim 8 wherein the catalyst/fatty acid molar ratio is comprised within a range of from 0.02 to 0.2.

15. The composition according to claim 1 wherein the one or more alkane-sulphonic acids, in addition to the methane-sulphonic acid, includes one or more, in any combination and in any mixture proportion, of ethane-sulphonic acid, n-propane-sulphonic acid, iso-propane-sulphonic acid, n-butanesulphonic acid, iso-butanesulphonic acid, sec-butane-sulphonic acid, tert-butanesulphonic acid.

16. The composition according to claim 1 wherein the one or more alkane-sulphonic acids is limited to the methane-sulphonic acid.

* * * * *